(12) United States Patent
Falkenberg et al.

(10) Patent No.: US 8,121,680 B2
(45) Date of Patent: Feb. 21, 2012

(54) SUBCUTANEOUS CARDIAC STIMULATION DEVICE PROVIDING ANTI-TACHYCARDIA PACING THERAPY AND METHOD

(75) Inventors: Eric Falkenberg, Las Vegas, NV (US); Mark W. Kroll, Crystal Bay, MN (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 436 days.

(21) Appl. No.: 12/113,895

(22) Filed: May 1, 2008

(65) Prior Publication Data

US 2008/0234769 A1 Sep. 25, 2008

Related U.S. Application Data

(63) Continuation of application No. 10/937,756, filed on Sep. 8, 2004, now Pat. No. 7,386,342.

(51) Int. Cl.
*A61N 1/39* (2006.01)

(52) U.S. Cl. .......................................................... 607/4

(58) Field of Classification Search ................ 607/5, 7, 607/9, 46, 63, 72, 4
See application file for complete search history.

(56) References Cited

U.S. PATENT DOCUMENTS

| | | | |
|---|---|---|---|
| 4,291,699 A | 9/1981 | Geddes et al. | |
| 5,562,708 A | 10/1996 | Combs et al. | |
| 5,817,131 A | 10/1998 | Elsberry et al. | |
| 5,830,236 A | 11/1998 | Mouchawar et al. | |
| 5,906,633 A * | 5/1999 | Mouchawar et al. | 607/5 |
| 6,167,305 A | 12/2000 | Cammilli et al. | |
| 6,405,081 B1 * | 6/2002 | Lyster et al. | 607/5 |
| 6,654,639 B1 | 11/2003 | Lu | |
| 6,711,442 B1 | 3/2004 | Swerdlow et al. | |
| 6,721,597 B1 | 4/2004 | Bardy et al. | |
| 6,772,007 B1 | 8/2004 | Kroll | |
| 7,069,075 B2 | 6/2006 | Olson | |
| 2002/0035376 A1 | 3/2002 | Bardy et al. | |
| 2002/0091414 A1 | 7/2002 | Bardy et al. | |
| 2002/0095184 A1 | 7/2002 | Bardy et al. | |
| 2002/0107544 A1 | 8/2002 | Ostroff et al. | |
| 2002/0107545 A1 | 8/2002 | Rissmann et al. | |
| 2002/0107547 A1 | 8/2002 | Erlinger et al. | |
| 2002/0107549 A1 | 8/2002 | Bardy et al. | |
| 2002/0120299 A1 | 8/2002 | Ostroff et al. | |
| 2003/0097153 A1 | 5/2003 | Bardy et al. | |

FOREIGN PATENT DOCUMENTS

WO 0222208 A2 3/2002

(Continued)

OTHER PUBLICATIONS

NonFinal Office Action, mailed Jun. 8, 2006: U.S. Appl. No. 10/937,756.

(Continued)

*Primary Examiner* — Eric D. Bertram

(57) ABSTRACT

An implantable subcutaneous cardiac device includes at least two subcutaneous electrodes adapted for placement external to a heart beneath the skin of a patient. The device further includes an arrhythmia detector that detects a sustained tachyarrhythmia of the heart and a pulse generator that delivers anti-tachycardia pacing pulses to the subcutaneous electrodes in response to detection of a sustained tachyarrhythmia. The pacing pulses preferably have waveforms devoid of any exponential voltage decay and include rounded or substantially constant portions to minimize pain.

21 Claims, 6 Drawing Sheets

FOREIGN PATENT DOCUMENTS

| | | |
|---|---|---|
| WO | 0222208 A3 | 3/2002 |
| WO | 0224275 A2 | 3/2002 |
| WO | 0224275 A3 | 3/2002 |
| WO | 03018124 A1 | 3/2003 |
| WO | 03039651 A2 | 5/2003 |
| WO | 03039665 A1 | 5/2003 |
| WO | 03039666 A1 | 5/2003 |
| WO | 03039667 A1 | 5/2003 |

OTHER PUBLICATIONS

NonFinal Office Action, mailed Nov. 15, 2006: U.S. Appl. No. 10/937,756.
Final Office Action, mailed Apr. 20, 2007: U.S. Appl. No. 10/937,756.
Advisory Action, mailed Jun. 18, 2007: U.S. Appl. No. 10/937,756.
NonFinal Office Action, mailed Jul. 27, 2007: U.S. Appl. No. 10/937,756.
Final Office Action, mailed Jan. 8, 2008: U.S. Appl. No. 10/937,756.
Notice of Allowance, mailed Mar. 10, 2008: U.S. Appl. No. 10/937,756.
NonFinal Office Action, mailed Nov. 16, 2006: U.S. Appl. No. 10/937,623.
Notice of Allowance, mailed May 17, 2007: U.S. Appl. No. 10/937,723.
NonFinal Office Action, mailed Jul. 14, 2006: U.S. Appl. No. 10/937,656.
Final Office Action, mailed Dec. 1, 2006: U.S. Appl. No. 10/937,656.
Notice of Allowance, mailed Apr. 18, 2007: U.S. Appl. No. 10/937,656.

\* cited by examiner

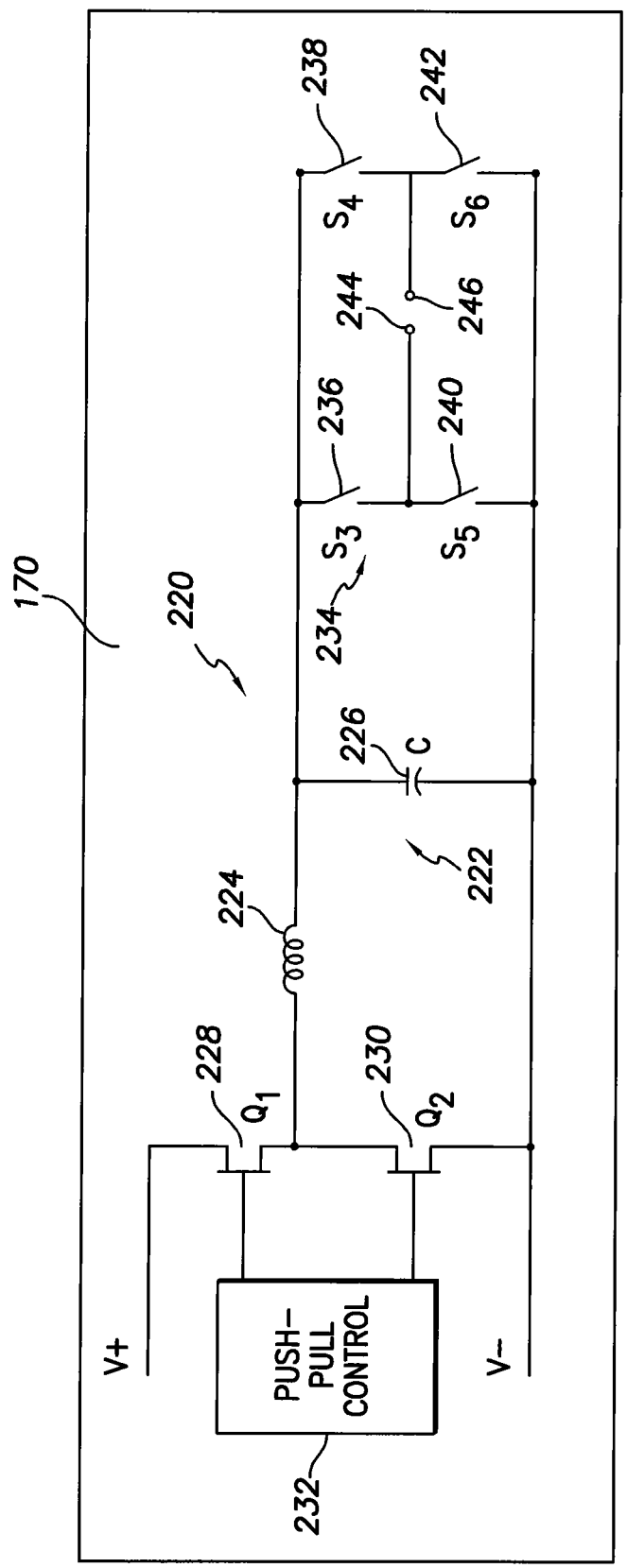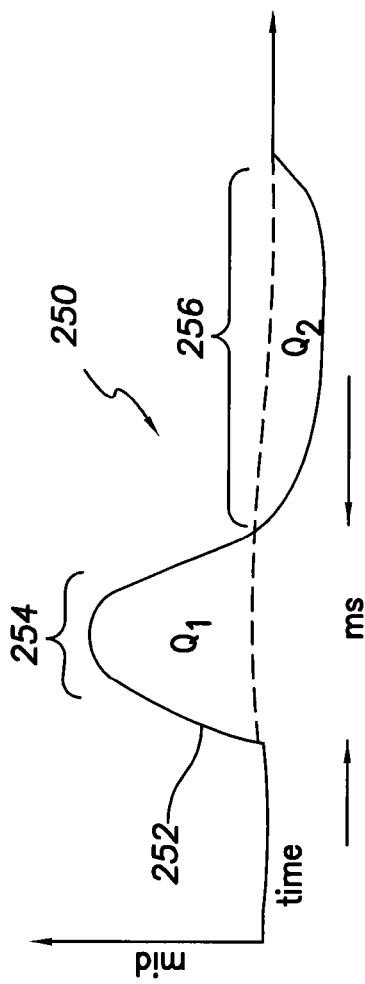
FIG. 4
FIG. 5

SUBCUTANEOUS CARDIAC STIMULATION DEVICE PROVIDING ANTI-TACHYCARDIA PACING THERAPY AND METHOD

CROSS-REFERENCE TO RELATED APPLICATIONS

This application is a continuation of U.S. patent application Ser. No. 10/937,756, titled "Subcutaneous Cardiac Stimulation Device Providing Anti-Tachycardia Pacing Therapy and Method," filed Sep. 8, 2004 and now U.S. Pat. No. 7,386,342, which is related to U.S. patent application Ser. No. 10/937,623, titled "Subcutaneous Cardiac Stimulation Device Providing Anti-Tachycardia Pacing Therapy and Method," filed Sep. 8, 2004 and now U.S. Pat. No. 7,277,755; and U.S. patent application Ser. No. 10/937,656, also titled "Subcutaneous Cardiac Stimulation Device Providing Anti-Tachycardia Pacing Therapy and Method," filed Sep. 8, 2004 and now U.S. Pat. No. 7,260,433.

FIELD OF THE INVENTION

The present invention generally relates to a cardiac stimulation device that provides electrical therapy to a patient's heart. The present invention more particularly relates to a subcutaneous device that provides anti-tachycardia pacing therapy while minimizing the perception of pain.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or evoked responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or evoked responses are sensed between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Subcutaneous cardiac stimulation devices are also known in the art. In these devices, the device enclosure may also be implanted beneath the skin of a patient. However, in these systems, the electrodes are not implanted within the heart. Rather, the electrodes may still be placed beneath the skin of the patient but external to the heart.

Subcutaneous cardiac devices are generally easier to implant. They are not generally relied on for providing long term pacing because the pacing efficiency of subcutaneous electrodes is low. In order to reliably pace, for example, stimulation pulse energies may be required which would rapidly deplete the battery of the device. Also of significance is the potential pain that may be caused by the required stimulation energies and electrode placement. However, subcutaneous cardiac stimulation devices may be advantageous for use in patients who do not require long term pacing, but who may have the potential to require sporadic cardiac stimulation therapy, such as for the abnormally high heart rate of an occasional tachyarrhythmia. Such conditions may be treated with anti-tachycardia pacing (ATP) to return the heart rate to a normal rate. Without such ATP, the heart rate may continue to accelerate into a more life threatening arrhythmia, such as ventricular fibrillation.

ATP is well known in the art. In such therapy, the heart is paced at a rate faster than the intrinsic rate. The heart beat is captured by the ATP and the pacing rate is gradually decreased to return the heart to a normal rate.

Even though subcutaneous cardiac stimulation devices are well suited for delivering ATP to a heart, the pain that such therapy may cause remains an issue. It is to this issue and the improved delivery of ATP with a subcutaneous cardiac stimulation device that the present invention more generally relates.

SUMMARY OF THE INVENTION

The invention provides an implantable subcutaneous cardiac device. The device comprises at least two subcutaneous electrodes adapted for placement external to a heart, and a pulse generator that delivers pacing pulses to the subcutaneous electrodes. The pacing pulses have a waveform devoid of any exponential voltage decay.

The invention further provides an implantable subcutaneous cardiac device comprising at least two subcutaneous electrodes adapted for placement external to a heart, and an arrhythmia detector that detects a sustained tachyarrhythmia of the heart. The device further comprises a pulse generator that delivers anti-tachycardia pacing pulses to the subcutaneous electrodes in response to detection of a sustained tachyarrhythmia.

The invention still further provides an implantable subcutaneous cardiac device comprising at least two subcutaneous electrodes adapted for placement external to a heart, a cardiac output monitor that monitors cardiac output, and an arrhythmia detector that detects a tachyarrhythmia of the heart. The device further comprises a pulse generator that delivers anti-tachycardia pacing pulses to the subcutaneous electrodes in response to detection of a tachyarrhythmia and a decrease in cardiac output.

The invention further provides a method comprising detecting a tachyarrhythmia of a heart with at least two subcutaneous electrodes external to the heart, and delivering anti-tachycardia pacing pulses to the subcutaneous electrodes. The pacing pulses having a waveform devoid of any exponential voltage decay.

The invention still further provides a method comprising detecting a sustained tachyarrhythmia of a heart with at least two subcutaneous electrodes external to the heart, and delivering anti-tachycardia pacing pulses to the subcutaneous electrodes responsive to detecting a sustained tachyarrhythmia. A sustained tachyarrhythmia may be a tachyarrhythmia accompanied by a decrease in cardiac output

BRIEF DESCRIPTION OF THE DRAWINGS

Further features and advantages of the present invention may be more readily understood by reference to the following description taken in conjunction with the accompanying drawings, in which:

FIG. 4 is a simplified schematic diagram of a pulse generator circuit according to an embodiment of the present invention;

FIG. 5 shows a waveform of a pacing pulse which may be provided by the circuit of FIG. 4;

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
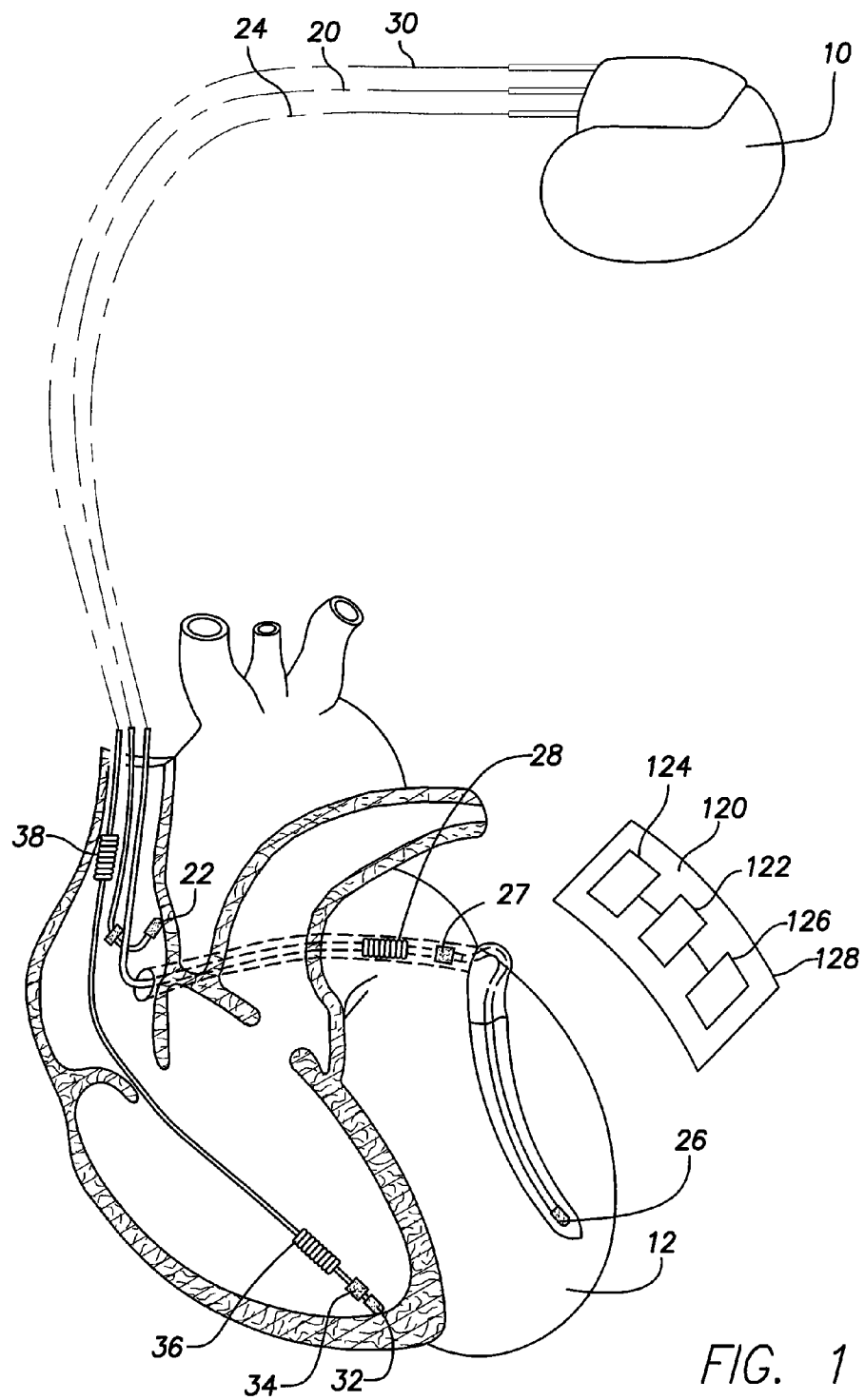
FIG. 1 is a simplified diagram illustrating a fully implantable stimulation device and a subcutaneous device in association with a patient's heart to be treated in accordance with the present invention.

As shown in FIG. 1, there is a fully implantable stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Also shown in FIG. 1 is a subcutaneous cardiac stimulation device 120. The device 120 includes an enclosure 122 which encloses the electronic circuitry of the device which will be described subsequently with reference to FIG. 3. The device 120 further includes electrodes 124 and 126. The electrodes 124 and 126 and the enclosure 122 are carried on a common substrate 128. The device 120 is a subcutaneous device because the electrodes 124 and 128 are placed beneath the skin of the patient but are external to the heart. The device 10, on the other hand, is fully implantable because its electrodes are not only beneath the skin of the patient, but are also implanted within the heart. The device 10 itself may be placed subcutaneously or submuscular.

The subcutaneous electrodes 124 and 126 may take the form of small patch electrodes. They may be employed for sensing electrical activity of the heart, delivering pacing pulses to the heart, and, if need be, providing cardioverting or defibrillating shocks to the heart.

FIG. 1 illustrates that both the fully implantable device 10 and the subcutaneous device 120 may both be implanted within a patient. The device 10 may be implanted in the left chest as is common in the art and the device 120 may be implanted so as to be over the bottom ribs of the patient. As will be seen hereinafter, the devices 10 and 120 may coordinate their operating in providing therapy, such as ATP to the heart. However, as will also be seen, the device 120 alone may be provided with sufficient functionality to enable it to provide ATP solely on its own.

Figure 2:
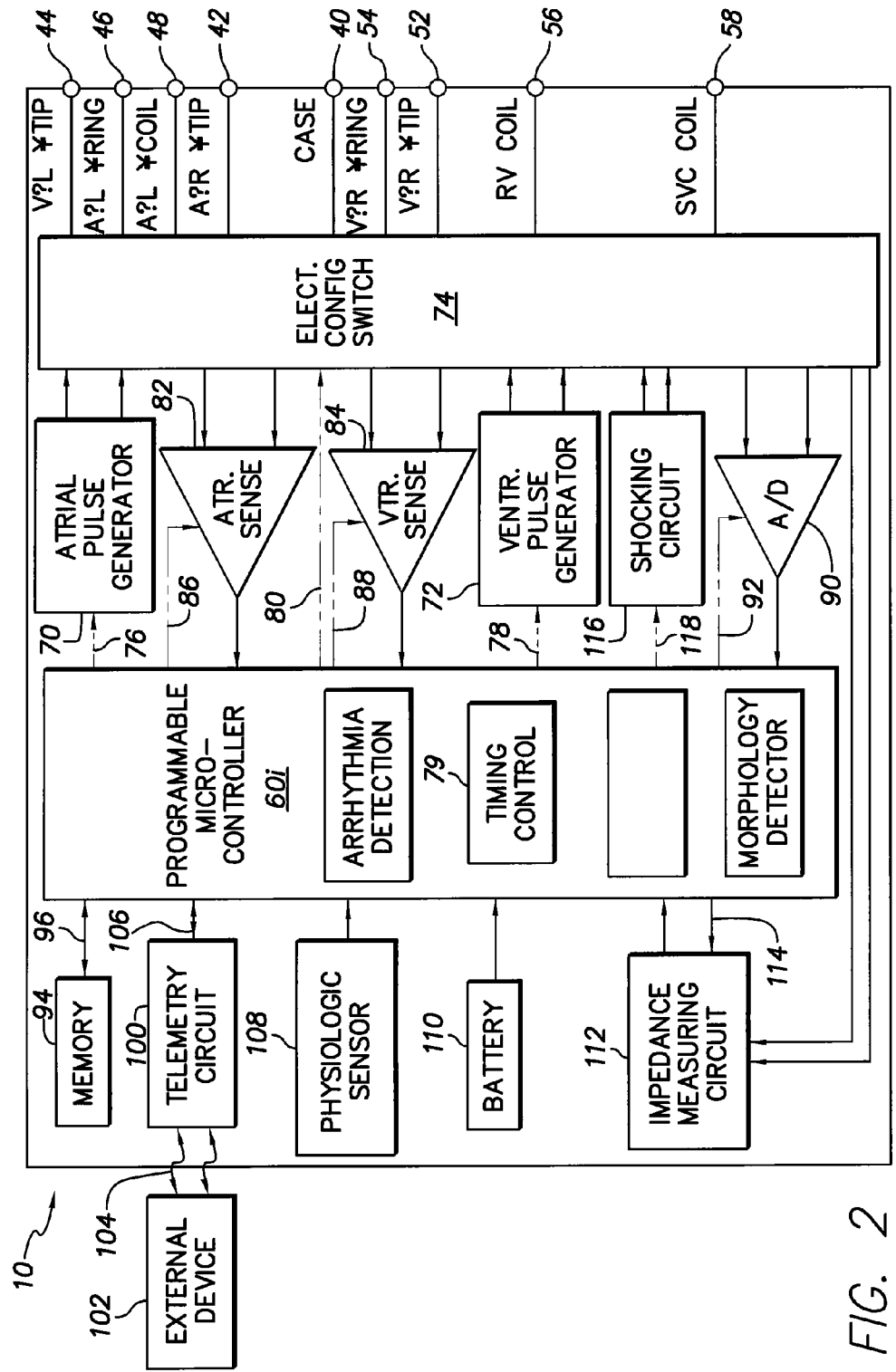
FIG. 2 is a functional block diagram of the fully implantable device taking the form of a multi-chamber implantable stimulation device capable of providing cardioversion, defibrillation and pacing stimulation in four chambers of the heart according to one embodiment of the invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. The telemetry circuit 100 may also be employed to support communication with the subcutaneous device 120. Through such communication, coordination between the devices in providing desired therapy may be maintained. Such coordination will be described subsequently.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

As will be seen hereinafter, the subcutaneous device 120 is fully capable of providing cardioverting/defibrillating therapy to the heart on its own. Hence, it is not necessary for the fully implantable device 10 to also provide such therapy. However, in the case where the stimulation device 10 is also intended to operate as an implantable cardioverter/defibrillator (ICD) device, it is preferable that it be able to detect the occurrence of an arrhythmia, and automatically apply an appropriate electrical shock therapy to the heart aimed at terminating the detected arrhythmia. To this end, the microcontroller 60 may further control a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
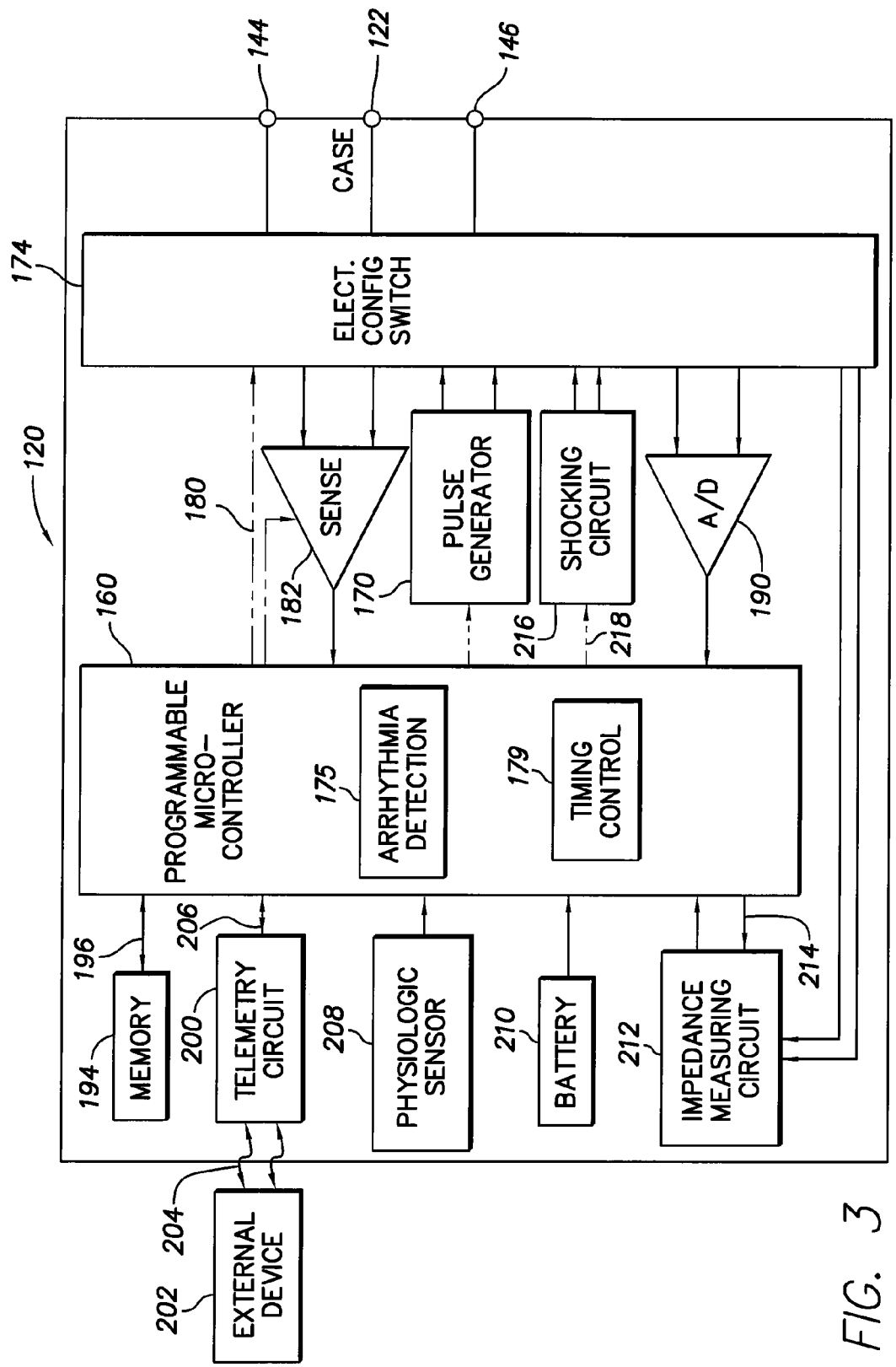
FIG. 3 is a functional block diagram of the subcutaneous device according to one embodiment of the present invention.

Referring now to FIG. 3, it is a simplified block diagram of the circuitry of the subcutaneous device 120, which may be enclosed within the enclosure 122.

The enclosure or case 122 for the stimulation device circuitry is shown schematically in FIG. 3 and may be conductive and programmably selected to act as the return electrode for "unipolar" pacing modes when desired. The enclosure 122 may further be used as a return electrode alone or in combination with one or more of the electrodes 124 and 128 for cardioversion or defibrillation purposes. The enclosure further includes a connector (not shown) having terminals 144 and 146 for connection to electrodes 124 and 126 respectively.

Also at the core of the subcutaneous stimulation device 120 is a programmable microcontroller 160 which controls the stimulation therapy. The microcontroller 160 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 160 includes the ability to process or monitor input signals (data) as controlled by a program code stored in a designated block of memory. The details of the design and operation of the microcontroller 160 are not critical to the present invention. Rather, any suitable microcontroller 160 may be used that carries out the functions described herein. The use of microprocessor-based control circuits for performing timing and data analysis functions are well known in the art.

As further shown in FIG. 3, a pulse generator 170 generates anti-tachycardia pacing stimulation pulses for delivery by one or more of electrodes 122, 124, and 126 via an electrode configuration switch 174. The microcontroller 60 further includes timing control circuitry 179 which is used to control the timing of such stimulation pulses.

The switch 174 includes a plurality of switches for connecting the desired electrodes to the appropriate I/O circuits. The switch 174 operates in response to a control signal 180 from the microcontroller 160 for making the desired electrode connections.

A sensing circuit 182 may also be selectively coupled to desired ones of the electrodes through the switch 174 for detecting the presence of cardiac activity. It may include dedicated sense amplifiers, multiplexed amplifiers, or shared amplifiers.

The sensing circuit 182 preferably employs one or more low power, precision amplifiers with programmable gain and/or automatic gain control, bandpass filtering, and a threshold detection circuit, as known in the art, to selectively sense the cardiac signal of interest. The automatic gain control thus enables the device 120 to reliably sense the ventricular cardiac activity to support detection of tachycardia and fibrillation. The output of the sensing circuit 182 is connected to the microcontroller 160.

The device 120 includes an arrhythmia detector 175 that utilizes the sensing circuit 182 to sense cardiac signals to determine whether a rhythm is physiologic or pathologic. Again, as used herein "sensing" is reserved for the noting of an electrical signal, and "detection" is the processing of these sensed signals and noting the presence of an arrhythmia. The timing intervals between sensed events are then classified by the microcontroller 160 by comparing them to predefined rate zone limits and various other characteristics including cardiac output in order to determine the presence of a sustained tachycardia, or fibrillation requiring anti-tachycardia pacing or cardioversion shocks or defibrillation shocks.

In accordance with this embodiment, the device 120 provides ATP therapy much later than a standard fully implantable device. For example, the device 120 may provide ATP therapy responsive to a sustained tachycardia characterized by tachycardia detection accompanied with a decrease in cardiac output instead of providing ATP upon the first detection of tachycardia.

Cardiac signals are also applied to the inputs of an analog-to-digital (A/D) data acquisition system 190. The data acquisition system 190 is configured to acquire intracardiac electrogram signals, convert the raw analog data into a digital signal, and store the digital signals for later processing and/or telemetric transmission to an external device 202. The data acquisition system 190 may be coupled through the switch 174 to sample cardiac signals across any pair of desired electrodes.

Advantageously, and in accordance with this embodiment, the data acquisition system 90 is coupled to the microcontroller for detecting an evoked response from the heart 12 in response to an applied ATP stimulus for detection of capture. The microcontroller 160 detects a depolarization signal during a window following an ATP stimulation pulse, the presence of which indicates that capture has occurred. The microcontroller 160 enables capture detection when the pulse generator 172 generates an ATP stimulation pulse. This starts a capture detection window using the timing control circuitry 79 within the microcontroller 60, and enables the data acquisition system 190 to sample the cardiac signal that falls in the capture detection window and, based on the amplitude, determines if capture has occurred. Capture detection may occur on a beat-by-beat basis or on a sampled basis. If an evoked response is not detected, the pulse generator output is preferably increased.

The microcontroller 160 is further coupled to a memory 194 by a suitable data/address bus 196, wherein the programmable operating parameters used by the microcontroller 60 are stored and modified, as required, in order to customize the operation of the subcutaneous stimulation device 120 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart.

Advantageously, the operating parameters of the implantable device 10 may be non-invasively programmed into the memory 194 through a telemetry circuit 200 in telemetric communication with the external device 202, such as a programmer, transtelephonic transceiver, or a diagnostic system analyzer. The telemetry circuit 200 is activated by the microcontroller by a control signal 206. The telemetry circuit 200 advantageously allows intracardiac electrograms and status information relating to the operation of the device 120 (as contained in the microcontroller 60 or memory 94) to be sent to the external device 202 through an established communication link 204.

In accordance with this embodiment, the telemetry circuit 200 may also be used for coordinating ATP therapy with a fully implanted device, such as device 10 of FIG. 1. In this regard, the telemetry circuit 200 may send a command to the fully implanted device to administer ATP therapy first before initiating therapy on its own. Hence, if the device 120 is informed by the fully implanted device 10 that it was unsuccessful at terminating the tachycardia, the subcutaneous device 120 may then take the therapy over and administer its ATP therapy.

Of course, the arrhythmia detector 175 of the subcutaneous device 120 could determine the success or failure of the implanted device 10 through its own arrhythmia detector 175.

Before the device 120 delivers ATP therapy, in accordance with this embodiment, it may administer electrical nerve stimulation such as that used in transcutaneous electrical nerve stimulation (TENS) to first treat the patient for possible pain caused by the ATP therapy. The electrical nerve stimulation (ENS) may be delivered from the pulse generator 172 to the electrodes 124 and 126 in the form of, for example, 5 to 10 volt pulses at 100 Hz. TENS is well known in the art.

In the preferred embodiment, the subcutaneous device 120 further includes a physiologic sensor 208, commonly referred to as a "rate-responsive" sensor. However, the physiological sensor 208 may be used to advantage in this embodiment to detect changes in cardiac output to support detection of a sustain tachycardia.

The subcutaneous device 120 additionally includes a battery 210 which provides operating power to all of the circuits shown in FIG. 3. The battery may again be lithium/silver vanadium oxide batteries.

Further in accordance with this embodiment, the device 120 is shown as having an impedance measuring circuit 212 which is enabled by the microcontroller 60 via a control signal 214. The impedance measuring circuit 212 may be used to advantage as an alternative measure in monitoring cardiac output. The impedance measuring circuit 212 is coupled to the switch 174 for selective coupling to electrodes 122, 124, and 126.

When the subcutaneous device 120 is called upon to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 216 by way of a control signal 218. The shocking circuit 216 generates shocking pulses of between 200 and 2,000 volts and more preferably between 500 and 1,000 volts for cardioversion/defibrillation. As used herein cardioversion is meant to be generic for both cardioversion and fibrillation. The shocking pulses are applied to the patient's heart 12 through at least two of the electrodes 122, 124, and 126.

Cardioversion shocks are provided if an ATP therapy is found to be unsuccessful. Additional tachyarrhythmia criteria may be imposed before a cardioversion shock is delivered.

Referring now to FIG. 4, it illustrates a schematic circuit diagram of a pulse generator 220 which may be used in pulse generator 170 for providing the ATP according to this embodiment of the present invention. The pulse generator 220 includes a filter 222 including an inductor 224 and a capacitor 226. The push-pull arrangement 232 of transistors 228 and 230 delivers a chopped full amplitude signal to the filter 222 formed by inductor 224 and capacitor 226. Representative chopping frequencies may be, for example, in the range of 5 to 20 kHz, but frequencies in the range of 1 to 300 kHz may also be used as well.

The filter 222 is coupled to an output H-bridge circuit 234 which is formed by solid state switches 236, 238, 240, and 242. The common junction of switches 236 and 240 form a first output terminal 244 and the common junction of switches 238 and 242 forms another output terminal 246.

The output H-bridge 234 will deliver a negative version of the signal coming out of filter 222 by turning on switches 238 and 240. A positive version of the signal coming out of the filter 222 is provided with the turning on of switches 236 and 242. The switches 236, 238, 240, and 242 may, for example, be FET transistors, as are known in the art.

The pulse generator 220 may be utilized for delivering ATP pulses to the electrodes 124 and 126, for example, for treating tachycardia with minimum pain.

FIG. 5 illustrates a pacing pulse 250 provided by the pulse generator 220 of FIG. 4 according to this embodiment of the present invention. The pacing pulse 250 has a generally rounded waveform 252 which, by virtue of the H-bridge 234, includes a first phase 254 and a second phase 256. As will be noted in FIG. 5, the waveform 252 is rounded in both the first phase 254 and the second phase 256 by virtue of the filter 222 of the pulse generator 220 and hence, is devoid of any exponential voltage decay. The first or positive phase 254 is fairly wide having a width, of, for example, 3 milliseconds. The rounded and very wide waveform of the first phase 254 will reduce nerve stimulation as nerves have a higher frequency response than do cardiac cells.

The second or negative phase 256 of the waveform 252 has about half of the voltage of the first or positive phase 254. The width of the second phase 256 is also about twice the width of the first phase 254.

Figure 6:
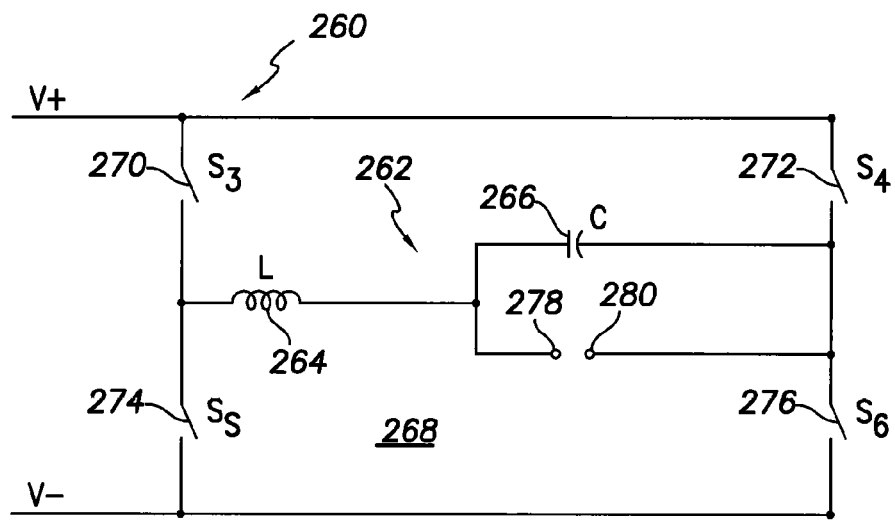
FIG. 6 is a simplified schematic diagram of another pulse generator circuit according to another embodiment of the present invention.

FIG. 6 is a simplified schematic diagram of another pulse generator 260 according to a further embodiment of the present invention. The pulse generator 260 includes a filter 262 including an inductor 264 and a capacitor 266. The filter 262 is within an H-bridge 268 formed by solid state switches 270, 272, 274, and 276. Again, the solid state switches 270, 272, 274, and 276 may be field effect transistors as known in the art.

The common junction of inductor 264 and capacitor 266 forms a first output terminal 278. The common junction of switches 272 and 276 forms the other output terminal 280.

Here, all of the waveform chopping is done within the bridge 268. Rather than having separate transistors perform the chopping function, and then have the H-bridge provide polarity inversion, the pulse generator 260 of FIG. 6 performs the waveform chopping by pulsing of the appropriate switches 270, 272, 274, and 276. This is then followed by the filtering effect of inductor 264 and capacitor 266 which are in parallel with the pacing electrodes.

Hence, the pulse generator 260 of FIG. 6 is capable of providing an output pacing pulse having a rounded waveform similar to that shown in FIG. 5. With appropriate control of switches 270, 272, 274, and 276, an output waveform having a rounded positive first phase and a rounded negative second phase, such as that shown in FIG. 5, may be provided to prevent nerve stimulation and thus pain.

Figure 7:
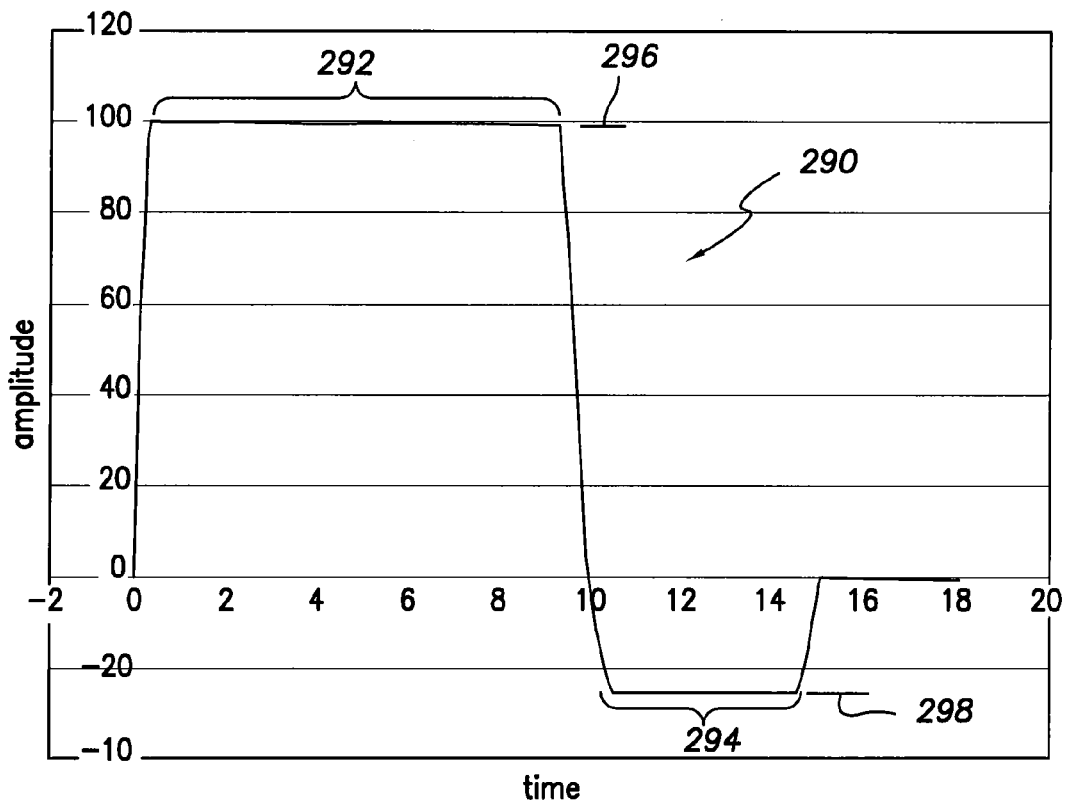
FIG. 7 is another waveform of a pacing pulse according to an embodiment of the invention.

FIG. 7 shows another pacing waveform 290 which may be employed to advantage in accordance with another embodiment of the present invention. The waveform 290 has been referred to as a plateau waveform and is fully described in copending application Ser. No. 10/855,840, filed May 26, 2004, titled "System and Method for Reducing Pain Associated with Cardioversion Shocks Generated by Implantable Cardiac Stimulation Devices," which is incorporated herein in its entirety by reference. The waveform 290 is biphasic and has a first phase 292 and a second phase 294. The first phase 292 is longer in duration than the second phase 294. The first phase 292 may have a duration of, for example, 10 milliseconds, as illustrated, but its duration may be in a range of, for example, 8 milliseconds to 12 milliseconds. The second phase 294 may have a duration of 5 milliseconds, as illustrated, but its duration may be in a range, for example, of 5 milliseconds to 8 milliseconds. The first phase 292 of the waveform 290 has a substantially constant or clamped positive amplitude 296 of, for example, 10 volts to 50 volts. The second phase 294 of the waveform 290 has a substantially constant or clamped negative amplitude 298 of, for example, 2 volts to 4 volts. It may be noticed in FIG. 7 that that waveform 290 is devoid of any exponential voltage decay characteristic of standard capacitive discharge waveforms. The waveform 290 has been found to substantially reduce the perception of pain when used to stimulate the heart as compared to standard capacitive discharge waveforms. Alternatively, the negative portion 294 of waveform 290 may be deleted as some arrhythmias appear to be better treated by monophasic instead of biphasic shocks.

Figure 8:
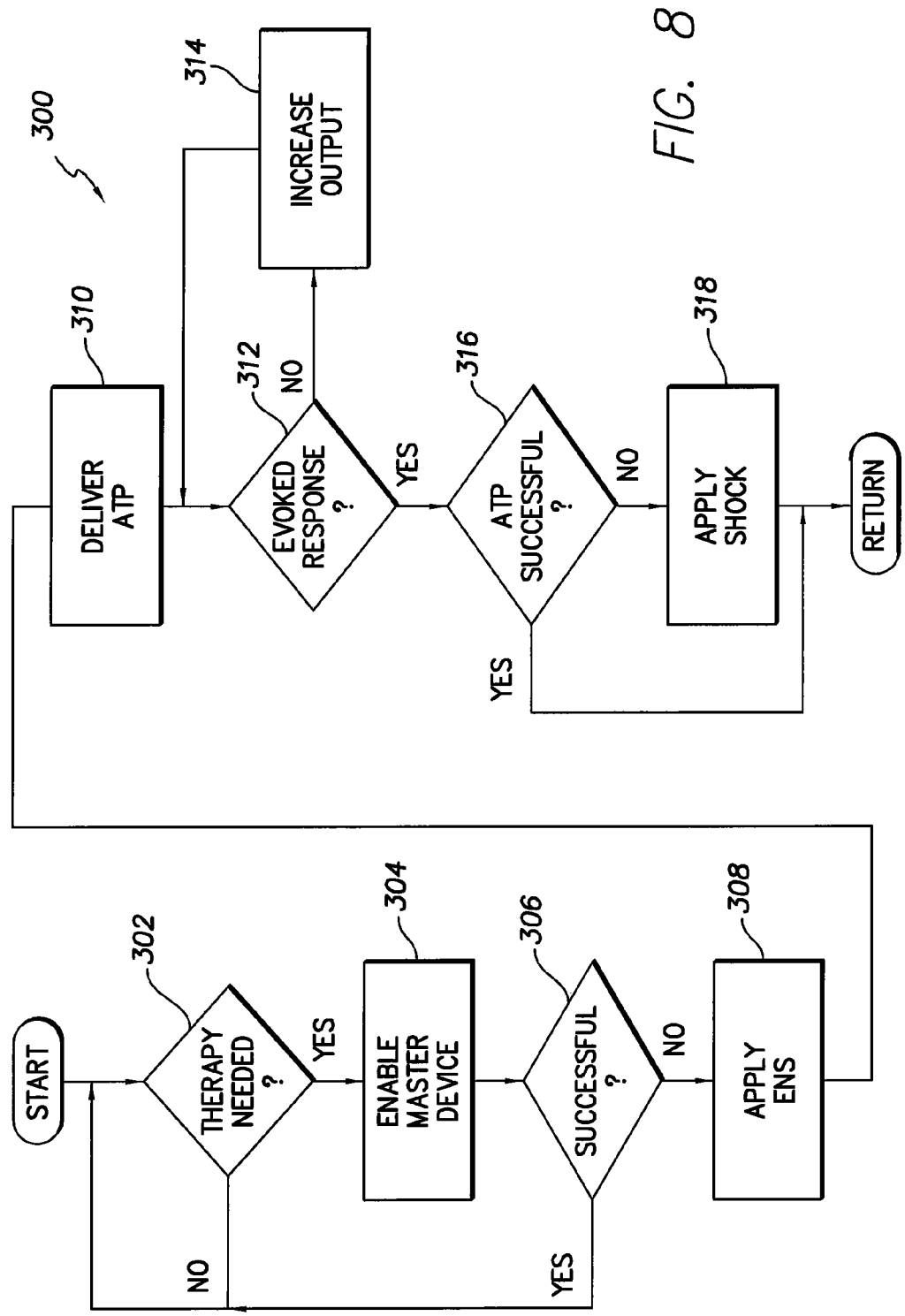
FIG. 8 is a flow chart describing an overview of the operation of one embodiment of the present invention.

In FIG. 8, a flowchart 300 is shown describing an overview of the operation and novel features implemented in one embodiment of the subcutaneous device 120. In this flowchart, the various algorithmic steps are summarized in individual "blocks." Such blocks describe specific actions or decisions that must be made or carried out as the algorithm proceeds. Where a microcontroller (or equivalent) is employed, the flowchart presented herein provides the basis for a "control program" that may be used by such a microcontroller (or equivalent) to effectuate the desired control of the stimulation device. Those skilled in the art may readily write such a control program based on the flow chart and other descriptions presented herein.

The process of the flowchart 300 initiates with a decision block 302. In decision block 302 it is decided if ATP therapy is required. To implement decision block 302, the arrhythmia detector 175 of the device 120 may utilize the electrogram generated by the sensing circuit 182 to determine if a ventricular tachycardia is present. The arrhythmia detector 175 may determine that therapy is required upon the onset of a detected ventricular tachycardia. Alternatively, the arrhythmia detector 175 may also condition the requirement for therapy upon evidence of a sustained ventricular tachycardia. In accordance with this alternative, the arrhythmia detector 175 may call upon the impedance measuring circuit 212, for example, to monitor for a decrease in cardiac output. Upon the detected ventricular tachycardia accompanied by a decrease in cardiac output, the arrhythmia detector 175 may declare a sustained ventricular tachycardia in need of therapy.

As an alternative to utilizing the impedance measuring circuit 212 for monitoring cardiac output, the arrhythmia detector 175 may call upon the physiologic sensor 208. The use of physiologic sensors for determining changes in cardiac output is well known in the art.

If therapy is not required, the process returns as illustrated. However, if therapy is needed in accordance with decision block 302, the process immediately advances to activity block 304 wherein the telemetry circuit 200 of the subcutaneous device 120 is utilized to communicate a command to the fully implanted device 10 to begin ATP therapy. The telemetry signal used may be a traditional radio frequency (RF) signal, an inductive signal, Galvanic signal or an acoustic signal. After the device 10 has delivered its ATP therapy, the process advances to decision block 306 to determine if the fully implanted device 10 was successful in terminating the ventricular tachycardia. If the device 10 was successful, the process returns. However, if the fully implanted device 10 was not successful in terminating the ventricular tachycardia, the process advances as described subsequently.

As an alternative to having the arrhythmia detector 175 determine if the fully implanted device 10 was successful in terminating the ventricular tachycardia, the fully implanted device 10 may make that determination on its own. Once the fully implanted device 10 has determined if it was successful, it would then communicate through its telemetry circuit 100 to the telemetry circuit 200 of the subcutaneous device 120 the status of the detected ventricular tachycardia. If the device 10 is successful in terminating the ventricular tachycardia, the message of success received by the telemetry circuit of the subcutaneous device 120 will cause the process of flowchart 300 to return. However, if the message from the implanted device 10 indicates that its efforts were unsuccessful, the subcutaneous device 120 will respond as indicated in flowchart 300 by advancing to activity block 308.

In activity block 308, the subcutaneous device 120 delivers electric nerve stimulation (ENS). In carrying out activity block 308, the subcutaneous device 120 may utilize its pulse generator 170 to provide electrical pulses to subcutaneous electrodes 124 and 128 for delivering the electrical nerve stimulation therapy. As previously mentioned, the electrical nerve stimulation therapy may be used to block pain and may take the form of electrical pulses at a rate of 100 Hz with amplitudes of 5 volts to 10 volts.

After the subcutaneous device 120 has delivered the electrical nerve stimulation therapy, the process then advances to activity block 310 wherein the subcutaneous device 120 delivers its ATP therapy. During delivery of the ATP therapy, as illustrated by the decision block 312, the subcutaneous device 120 continuously detects for evoked responses to the pacing pulses of the ATP therapy being delivered by the pulse generator 170 of the subcutaneous device 120. If there is a failure to detect evoked responses, the process advances to activity block 314 wherein the output of the pacing pulses is increased. Hence, if there is a failure to capture the heart during the ATP therapy, the output of the pacing pulses is increased until the heart is captured.

When the ATP therapy is completed, the process then advances to decision block 316 where it is determined if the ATP therapy was successful. If the ATP therapy was successful, the process returns. If the ATP therapy delivered by the subcutaneous device 120 is not successful in not terminating the ventricular tachycardia, the process then advances to activity block 318 to apply a cardioverting or defibrillating shock to electrodes 124 and 128. Once the cardioverting or defibrillating shock is applied to the heart, the process returns.

Instead of the subcutaneous device 120 delivering the cardioverting or defibrillating shock, it may alternatively communicate a command through its telemetry circuit 200 to the implanted device 10 to cause it to deliver the cardioverting or defibrillating shock using its implanted shock electrodes. The subcutaneous device 120 may either detect the delivery of the cardioverting or defibrillating shock by the fully implanted device 10 or wait until it receives a communication from the device 10 through its telemetry circuitry before causing the process of flowchart 300 to return. Of course, if the patient does not have a fully implanted device as, for example, device 10, requiring the subcutaneous device 120 to operate on its own, it will of course perform the electrical nerves stimulation and ATP therapy immediately upon determining that therapy is needed and will also apply the cardioverting or defibrillating shock if its ATP therapy is unsuccessful in terminating the ventricular tachycardia.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable subcutaneous cardiac device comprising:
   at least two subcutaneous electrodes adapted for placement near a heart but neither in nor on a heart and not in a vein associated with the heart; and
   a pulse generator that delivers a pacing pulse to the subcutaneous electrodes, the pacing pulse having a waveform consisting of a positive phase devoid of any exponential voltage decay and a negative phase devoid of any exponential voltage decay, wherein the positive phase initiates at a baseline voltage and includes a first portion curving away from the baseline voltage toward a peak voltage and a second portion curving along its entire length away from the peak voltage back to the baseline voltage, wherein the baseline voltage is the voltage level at which the positive phase transitions to the negative phase;
   wherein the positive phase and the negative phase are each defined by a rounded waveform having a width and a peak voltage, the peak voltage of the rounded waveform defining the positive phase is greater than the peak voltage of the rounded waveform defining the negative phase, and the width of the rounded waveform defining the positive phase is less than the width of the rounded waveform defining the negative phase.

2. The device of claim 1 wherein the pulse generator provides anti-tachycardia pacing pulses.

3. The device of claim 2 wherein the pulse generator provides electrical nerve stimulation pulses prior to providing the pacing pulses.

4. The device of claim 3 wherein the pulse generator provides the nerve stimulation pulses to the at least two subcutaneous electrodes.

5. The device of claim 2 further comprising an arrhythmia detector that detects a tachyarrhythmia of the heart and wherein the pulse generator delivers anti-tachycardia pacing pulses to the subcutaneous electrodes in response to detection of a tachyarrhythmia.

6. The device of claim 5 wherein the device causes a cardioversion shock to be delivered to the heart when the arrhythmia detector detects a tachyarrhythmia after delivery of the anti-tachycardia pacing pulses.

7. The device of claim 6 further comprising a telemetry circuit that enables a fully implanted stimulation device to provide the cardioversion shock.

8. The device of claim 6 further comprising a shocking circuit that provides the cardioversion shock.

9. The device of claim 2 further comprising a telemetry circuit that enables a fully implanted stimulation device to provide anti-tachycardia pacing pulses to the heart before the pulse generator delivers anti-tachycardia pacing pulses.

10. The device of claim 1 further comprising an evoked response detector that detects for evoked responses from the pacing pulses and wherein the pulse generator provides an increased pacing output responsive to a failure to detect the evoked responses.

11. The device of claim 1 wherein the peak voltage of the positive phase is about twice the peak voltage of the negative phase.

12. The device of claim 1 wherein the width of the positive phase is about half the width of the negative phase.

13. The device of claim 1 wherein the negative phase includes a first portion curving away from the baseline voltage toward a peak negative voltage and a second portion curving along its entire length away from the peak negative voltage to the baseline voltage.

14. A method comprising:
detecting a tachyarrhythmia of a heart with at least two subcutaneous electrodes near a heart but neither in nor on a heart and not in a vein associated with the heart; and
delivering anti-tachycardia pacing pulses to the subcutaneous electrodes, the pacing pulses having waveforms consisting of a positive phase devoid of any exponential voltage decay and a negative phase devoid of any exponential voltage decay, wherein the positive phase initiates at a baseline voltage and includes a first portion curving away from the baseline voltage toward a peak voltage and a second portion curving along its entire length away from the peak voltage back to the baseline voltage, wherein the baseline voltage is the voltage level at which the positive phase transitions to the negative phase, wherein the positive phase and the negative phase are each defined by a rounded waveform having a width and a peak voltage, the peak voltage of the rounded waveform defining the positive phase is greater than the peak voltage of the rounded waveform defining the negative phase, and the width of the rounded waveform defining the positive phase is less than the width of the rounded waveform defining the negative phase.

15. The method of claim 14 further comprising applying nerve stimulation pulses to the at least two subcutaneous electrodes prior to delivering the anti-tachycardia pacing pulses.

16. The method of claim 14 further comprising redetecting for a tachyarrhythmia following delivery of the anti-tachycardia pacing pulses and applying a cardioversion shock to the heart responsive to redetecting a tachyarrhythmia.

17. The method of claim 16 wherein applying comprises commanding a fully implanted cardiac stimulation device to apply the cardioversion shock.

18. The method of claim 14 further comprising detecting for evoked responses to the anti-tachycardia pacing pulses and increasing stimulation energy of the pacing pulses responsive to failing to detect evoked responses.

19. The method of claim 14 further comprising applying anti-tachycardia pacing pulses to the heart with intracardiac electrodes before delivering the anti-tachycardia pacing pulses to the subcutaneous electrodes.

20. The method of claim 14 wherein the negative phase includes a first portion curving away from the baseline voltage toward a peak negative voltage and a second portion curving along its entire length away from the peak negative voltage to the baseline voltage.

21. An implantable cardiac device comprising:
at least two electrodes adapted for placement in, on or near a heart; and
a pulse generator that delivers a pacing pulse to the electrodes, the pacing pulse having a waveform consisting of a positive phase devoid of any exponential voltage decay and any truncation, and a negative phase devoid of any exponential voltage decay and any truncation, the positive phase including a first portion curving away from a baseline voltage toward a peak voltage and a second portion curving along its entire length away from the peak voltage back to the baseline voltage;
wherein the positive phase and the negative phase are each defined by a rounded waveform having a width and a peak voltage, the peak voltage of the rounded waveform defining the positive phase is greater than the peak voltage of the rounded waveform defining the negative phase, and the width of the rounded waveform defining the positive phase is less than the width of the rounded waveform defining the negative phase.

* * * * *